US007456300B2

(12) United States Patent
Watanabe et al.

(10) Patent No.: US 7,456,300 B2
(45) Date of Patent: Nov. 25, 2008

(54) PROCESS OF PRODUCING DIOXANE GLYCOL

(75) Inventors: Masafumi Watanabe, Okayama (JP); Junichi Amemiya, Okayama (JP); Ikutaro Kuzuhara, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 105 days.

(21) Appl. No.: 11/542,274

(22) Filed: Oct. 4, 2006

(65) Prior Publication Data

US 2007/0078271 A1 Apr. 5, 2007

(30) Foreign Application Priority Data

Oct. 4, 2005 (JP) .............................. 2005-291613

(51) Int. Cl.
*C07D 319/06* (2006.01)
(52) U.S. Cl. ...................................... 549/374
(58) Field of Classification Search .................. 549/374
See application file for complete search history.

(56) References Cited

U.S. PATENT DOCUMENTS 2,945,008 A 7/1960 Caldwell et al.

FOREIGN PATENT DOCUMENTS

JP 59 134788 A 8/1984

OTHER PUBLICATIONS

Galiano, F.R., et al.; "Formation of 1, 3-Dioxanes in Water" Journal of Organic Chemistry, vol. 29, No. 11, 1964, pp. 3424-3426.
Extended European Search Report for EP 06121253.6, mailed Jan. 30, 2007.

*Primary Examiner*—Bernard Dentz
(74) *Attorney, Agent, or Firm*—Antonelli, Terry, Stout & Kraus, LLP.

(57) ABSTRACT

A process of producing 2-(5-ethyl-5-hydroxymethyl-1,3-dioxane-2-yl)-2-methylpropane-1-ol (DOG) by the acetalization of hydroxypivalaldehyde with trimethylolpropane in water in the presence of an acid catalyst and optional seed crystals. DOG crystals having an increased particle size and containing the trans isomer in a high content are produced by the process in which the reaction temperature, pH of the reaction system and concentration of DOG to be produced in the reaction system are controlled.

15 Claims, No Drawings

PROCESS OF PRODUCING DIOXANE GLYCOL

BACKGROUND OF THE INVENTION

1. Field of the Invention

The present invention relates to a process of producing 2-(5-ethyl-5-hydroxymethyl-1,3-dioxane-2-yl)-2-methyl-propane-1-ol (hereinafter referred to as "dioxane glycol" or "DOG"), which is represented by the following formula I:

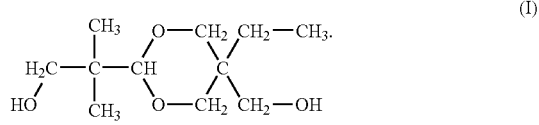

2. Description of the Prior Art

DOG is produced, for example, by a process including the acetalization of hydroxypivalaldehyde (hereinafter referred to as "HPA") represented by the following formula II:

with trimethylolpropane (hereinafter referred to as "TMP") represented by the following formula III:

in the presence of an acid catalyst; the neutralization of the resultant reaction product liquid; and the filtration, washing and drying of the deposited DOG crystals (JP 62-59104B).

The acetalization under acidic condition is generally an equilibrium reaction, and DOG produced undergoes decomposition. Therefore, a solvent having a low solvent power to DOG such as water is generally used to deposit DOG as crystals immediately after its formation, thereby shifting the equilibrium toward the product side. Even when the solvent power to DOG is low, DOG dissolves in the solvent to some extent if a raw material such as TMP is dissolved in the solvent, thereby failing to prevent the decomposition of DOG. To reduce the amount of DOG dissolved in the mother liquor, the acetalization can be performed at lower temperatures or the solvent can be used in a large amount. However, these measures are industrially disadvantageous, because the acetalization becomes slow if the temperature is lowered and the use of a large amount of solvent requires great costs for the treatment of waste water.

In the production of DOG by a known method as disclosed in JP 62-59104B, the amount of waste water such as filtrates and washings after recovering DOG reaches about 10 times the amount of DOG produced. In addition, the yield is as low as 70 to 85 mol % and a considerable amount of the non-reacted raw materials and reaction intermediates remain in the reaction mother liquor after recovering the crystals. Therefore, the known method involves high environmental load in consideration of the treatment of waste water and waste products and the energy consumption.

DOG produced by a known method as disclosed in JP 62-59104B can be purified into a high purity DOG by recrystallization from an organic solvent. However, this is industrially disadvantageous because the number of steps for the production of DOG is significantly increased.

To reduce the amount of waste water and improve the yield, the filtrate can be reused in the next run of reaction. However, in a production method including a step of neutralizing the reaction product liquid with alkali after the reaction, a large amount of the acid catalyst is needed in the next run of reaction and the slats formed by the neutralization accumulate in the mother liquor during repeated reuse.

DOG crystals can be obtained by filtration directly after the reaction without neutralization with alkali, and the subsequent washing with water and drying. However, DOG produced by a known method decomposes upon heating for the production of polymer materials, etc., to deteriorate the properties of the product being produced.

In addition, the particle size of DOG produced by a known method as disclosed in JP 62-59104B is extremely small to make the handling thereof difficult.

DOG has the following two isomers: trans isomer and cis isomer.

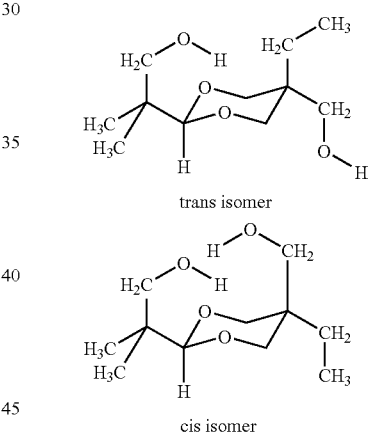

DOG or its derivative having a high content of the trans isomer (hereinafter referred to as "high trans-isomer purity" or merely "high purity") is preferably used as the raw material for industrial production. However, DOG produced by a known method contains a considerable amount of the cis isomer.

Known documents relating to the production of DOG are completely silent about the trans-isomer purity of DOG. As a result of extensive studies by the inventors, it has been found that DOG produced by known methods has a low trans-isomer purity, although mainly composed of the trans isomer. For example, the highest melting point of DOGs actually disclosed in the working examples of JP 62-59104B is 121.5° C. However, a purified DOG having a trans-isomer purity of 99% or more, which is obtained by the recrystallization from acetone of DOG having such highest melting point, shows a melting point of 125° C. or higher. The term "trans-isomer purity" referred to herein is the proportion (% by weight) of the trans isomer to the total weight of DOG.

SUMMARY OF THE INVENTION

An object of the present invention is to solve the problems associated with the conventional techniques and to provide an industrially advantageous process of producing a high purity DOG having an adequately large crystal particle size. Another object is to provide a process of producing DOG which is capable of improving the heat stability of DOG and reducing the amount of waste water.

As a result of extensive research, the inventors have found that DOG having an increased particle size can be produced by a process in which the reaction temperature, the pH of reaction system and the amounts of raw materials in the reaction system are controlled. It has been also found that the heat stability of DOG can be drastically improved by separating DOG crystals produced by the above process and then washing the separated DOG crystals with a basic solution. It has been further found that not only the amount of waste water can be reduced, but also the yield of DOG is increased and a high purity DOG can be produced by reusing a limited amount of the mother liquor obtained in the above process in the next and subsequent runs of the DOG synthesis (also referred to as the reaction of HPA and TMP or acetalization of HPA). It has been still further found that the particle size of DOG can be increased by performing the DOG synthesis in the presence of a specific amount of seed crystals. The present invention is based on these findings.

Thus, the present invention provides a process of producing a dioxane glycol represented by the following formula I:

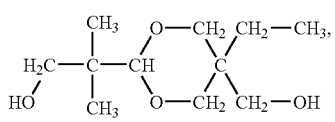
(I)

which includes a step of allowing hydroxypivalaldehyde represented by the following formula II:

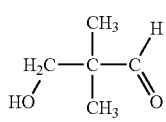
(II)

to react with trimethylolpropane represented by the following formula III:

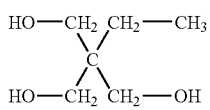
(III)

in water in the presence of an acid catalyst, the reaction of hydroxypivalaldehyde and trimethylolpropane being performed under conditions which meet the following requirements:

(A) a total amount of amines and/or amine salts in hydroxypivalaldehyde is 1.5% by weight or less;

(B) the reaction is performed at from 65 to 80° C;

(C) pH of a reaction system is kept within a range of from 0.1 to 4.0 during the reaction;

(D) X represented by the following formula IV:

$$X(\% \text{ by weight})=B/A\times100 \tag{IV}$$

wherein A is a total weight of hydroxypivalaldehyde, trimethylolpropane, the acid catalyst, and water which are supplied to the reaction system, and B is a theoretical amount of the dioxane glycol to be produced from hydroxypivalaldehyde and trimethylolpropane which are supplied to the reaction system, is from 3 to 35% by weight; and (E) a solid or solution of hydroxypivalaldehyde is added to trimethylolpropane, water and the acid catalyst which are charged in a reaction vessel over 0.5 to 24 h.

DETAILED DESCRIPTION OF THE INVENTION

In the present invention, DOG is produced by the reaction of TMP and HPA in the presence of an acid catalyst, preferably in the presence of the acid catalyst and an optional seed crystals. The reaction is preformed in water and/or an organic solvent, preferably in water. Examples of the organic solvent include methanol, ethanol and acetone. Commercially available TMP may be used as-purchased or after purification by distillation or crystallization.

HPA may be used as-synthesized or may be used after purification by crystallization from water, etc. Since HPA is synthesized by the reaction of isobutylaldehyde and formaldehyde in the presence of an amine catalyst, the synthesized HPA contains amines and/or amine salts. The total amount of the amines and/or amine salts in HPA is preferably 1.5% by weight or less, more preferably 0.5% by weight or less, and still more preferably 0.1% by weight or less (each inclusive of zero). If exceeding 1.5% by weight, the amount of the acid catalyst required in the synthesis of DOG increases, and in addition, the trans-isomer purity of DOG is lowered and the particle size of DOG is reduced because of the salting-out effect. Such problems become considerable when the reaction mother liquor after separation of DOG crystals is reused. The amine catalyst is preferably triethylamine. If triethylamine is used, the resultant HPA contains triethylamine and/or triethylammonium formate. The content of formaldehyde in HPA is preferably 2.2% by weight or less and more preferably 0.1% by weight or less. Since formaldehyde is reactive with TMP, a large amount of remaining formaldehyde increases the amount of by-products.

The molar ratio, HPA/TMP, is preferably from 0.3 to 2.5 and more preferably from 0.8 to 1.5. When being 2.5 or less, the side reaction such as decomposition of excess HPA and dimerization of HPA is prevented, and the increase of the material unit of HPA (amount of HPA required for the production of a unit amount of DOG) and the reduction of the purity of DOG are avoided. DOG is highly soluble in a solution rich in TMP, and therefore, a substantial portion of the produced DOG comes to dissolve in the mother liquor to drastically reduce the yield of DOG, if TMP is used in an excessively large amount as compared with HPA. This problem can be avoided when HPA/TMP is 0.3 or more.

Examples of the acid catalyst include, but not limited to, mineral acids such as hydrochloric acid, sulfuric acid, phosphoric acid and nitric acid, and organic acids such as benzenesulfonic acid, toluenesulfonic acid and methanesulfonic acid, with the organic acids being particularly preferred, and toluenesulfonic acid and methanesulfonic acid being more preferred. The amount of the acid catalyst to be used in the reaction depends upon its kind, and is selected so as to maintain the pH of the reaction system in a range preferably from 0.1 to 4.0 and more preferably from 1.0 to 2.0. Within the above range, the corrosion of apparatus and decrease in the reactivity are prevented, and the reductions in the yield and trans-isomer purity of DOG are prevented.

The reaction temperature is preferably from 65 to 80° C. and more preferably from 68 to 75° C. The variation of temperature during the reaction is preferably controlled within ±2° C. Within the above range, the reaction time does not become so long and DOG having a high trans-isomer purity is produced in high yields without causing problems such as formation of oily DOG, degradation of DOG, and decrease of the crystal particle size which increases the liquid content of wet crystals. Although the reaction pressure is not specifically limited, it is industrially practical to perform the reaction under atmospheric pressure.

In the present invention, HPA, TMP, acid catalyst, and water are supplied to the reaction system so as to regulate X represented by the following formula IV:

$$X(\% \text{ by weight}) = B/A \times 100 \quad \text{(IV)}$$

wherein A is the total weight of HPA, TMP, the acid catalyst, and water which are supplied to the reaction system, i.e., the total weight of the reaction product liquid at the time the synthesis of DOG is completed, and B is a theoretical amount of DOG to be produced from HPA and TMP which are supplied to the reaction system, within a range of preferably from 3 to 35% by weight and more preferably from 10 to 20% by weight. X corresponds to the concentration of DOG in the reaction product liquid when the DOG synsthesis proceeds theoretically. When X is 3% by weight or more, the production amount of DOG per a single run of reaction is sufficient. When being 35% by weight or less, the crystal concentration in the reaction product solution is moderate for a sufficient stirring of the reaction system, to increase the trans-isomer purity and particle size of DOG.

The synthesis of DOG may be performed in the presence of optional seed crystals in addition to the acid catalyst. The seed crystals are mainly composed of DOG, and preferably DOG itself. DOG obtained through solid-liquid separation, washing, drying, etc. may be used as the seed crystals. Alternatively, a part of the reaction product liquid (slurry) at the time the DOG synthesis is completed may be also used as the seed crystals without further treatment. In case of using the seed crystals, HPA, TMP, acid catalyst, water, and seed crystals are supplied to the reaction system so as to regulate, in place of X in the formula IV, X' represented by the following formula V:

$$X'(\% \text{ by weight}) = B'/A' \times 100 \quad \text{(V)}$$

wherein A' is the total weight of HPA, TMP, the acid catalyst, seed crystals, and water which are supplied to the reaction system, i.e., the total weight of the reaction product liquid at the time the DOG synthesis in the presence of the seed crystals is completed, and B' is the total weight of a theoretical amount of DOG to be produced from HPA and TMP which are supplied to the reaction system and the amount of DOG contained in the seed crystals added, within a range of preferably from 3 to 35% by weight and more preferably from 10 to 20% by weight. X' corresponds to the concentration of the total DOG (DOG produced and DOG contained in the seed crystals) in the reaction product liquid when the DOG synthesis in the presence of the seed crystals proceeds theoretically.

The amount the seed crystals, if used, is preferably from 0.1 to 30% by weight and more preferably from 2 to 5% by weight based on the total weight of HPA, TMP, the acid catalyst, seed crystals and water. Within the above range, the effect of increasing the particle size and purity of DOG due to the addition of the seed crystals is obtained without reducing the production amount of DOG per a single run of reaction. The seed crystals may be charged all at once in a reaction vessel at the time of the reaction is initiated, or may be added through the reaction, for example, from the beginning of the reaction to an appropriate stage before the completion of the reaction.

The DOG synthesis is preferably performed in the following methods:

(1) Method in which TMP, acid catalyst, optional seed crystals, and water are all charged in a reaction vessel and heated to a predetermined temperature (reaction temperature), to which HPA (solid or solution) is continuously added;

(2) Method in which HPA (solid or solution), acid catalyst, optional seed crystals, and water are all charged in a reaction vessel and heated to a predetermined temperature (reaction temperature), to which TMP (solid or solution) is continuously added; and (3) Method in which a part of HPA (solid or solution), a part of TMP (solid or solution), acid catalyst, optional seed crystals, and water are all charged in a reaction vessel and heated to a predetermined temperature (reaction temperature), to which the rest of HPA (solid or solution) and the rest of TMP (solid or solution) are continuously added, with the method 1 being preferred.

The addition of HPA, TMP or the rest of HPA and TMP in the above methods is performed preferably over 0.5 to 24 h and more preferably over 1 to 12 h. If the addition is performed within the above range, the crystal particle size and trans-isomer purity are increased without spending much time and causing a violent reaction. After the addition, the reaction product liquid may be aged at a temperature nearly the same as the reaction temperature preferably for 0.5 to 12 h, more preferably for 1 to 8 h, and still more preferably for 1.5 to 6 h.

DOG produced by the reaction deposits as crystals in the reaction product liquid, from which DOG crystals are separated by solid-liquid separation such as filtration and centrifugal separation. The solid-liquid separation is conducted on the reaction product liquid having a pH of preferably from 0.1 to 4.0 and more preferably from 1.0 to 2.0 without neutralizing the reaction product liquid. DOG crystals produced by the present invention are easy to handle because of their adequately large particle size and its wet form has a liquid content as low as less than 30% by weight.

The reaction mother liquor obtained by separating DOG crystals from the reaction product liquid contains a large amount of the acid catalyst, DOG, and unreacted HPA and TMP. In the present invention, the reaction mother liquor may be reused in the next and subsequent runs of reaction in an amount of preferably 98% by weight or less, more preferably from 70 to 98% by weight, and still more preferably from 70 to 90% by weight. If exceeding 98% by weight, impurities are accumulated in the mother liquor until they contaminate DOG crystals to reduce the trans-isomer purity.

DOG crystals separated from the reaction product liquid are preferably washed with a basic solution. By the washing with the basic solution, the mother liquor held in DOG crystals and the acid catalyst adhered to the surface of crystals are neutralized. Also, the base can be provided to DOG crystals in an amount enough to neutralize the acid to be generated by the thermal decomposition of DOG. The basic solution is prepared by dissolving the base in water and/or an organic solvent such as methanol, ethanol and acetone. The solvent for the basic solution is preferably the same as the solvent used in the DOG synthesis.

Examples of the base include inorganic bases such as lithium carbonate, lithium hydrogencarbonate, magnesium carbonate, sodium hydrogencarbonate, potassium hydrogencarbonate, sodium carbonate, potassium carbonate, sodium hydroxide, potassium hydroxide, sodium phosphate, potassium phosphate, calcium carbonate, calcium hydroxide and barium carbonate; and organic bases such as diethylamine and triethylamine, with inorganic bases being preferred because products having good properties with less discoloration and odor can be produced from DOG. The base concentration of the basic solution is preferably from 10 ppm to 50% by weight and more preferably from 0.01 to 10% by weight.

The washing is effected by a method in which the mother liquor in DOG crystals is allowed to homogeneously mix with the basic solution under stirring, or a method in which the basic solution uniformly sprayed on the surface of DOG crystals is forced to penetrate into DOG crystals by applying a pressure or centrifugal force. The basic solution is used preferably in an amount such that the base is from 1.001 to 10 times the mole of the acid catalyst in the separated DOG crystals. The amount of the acid catalyst in the separated DOG crystals is determined, for example, by adding distilled water to an amount of DOG crystals to make the distilled water and the mother liquor in the DOG crystals into a homogeneous mixture; filtering; and then titrating the filtrate with an alkali. In case of reusing the mother liquor, the amount of the acid catalyst in DOG crystals can be calculated from the yield of DOG, the amount of separated DOG crystals, the charged amount of acid catalyst, etc. After washing with the basic solution, the basic solution is recovered by filtration or centrifugal separation. It is more preferred to use the basic solution in such an amount that the pH of the recovered basic solution is 8 or higher.

It is preferred that DOG crystals after washing with the basic solution have the same liquid content as that of DOG crystals before washing. The liquid content is generally from 5 to 60% by weight, although varies depending upon the particle size and shape of crystals. After washing with the basic solution, DOG crystals may be further washed with water, etc.

DOG crystals which have been obtained through washing with water or an organic solvent, drying, etc. without being washed with the basic solution can be also improved in the heat stability by the washing with the basic solution. Such washing can be made by stirring a mixture of DOG crystals and the basic solution so as to form a uniform slurry.

DOG crystals thus washed with the basic solution may be dried without further treatment or after being melted and made into lumps, flakes, etc., to obtain final products.

The present invention will be described in more detail. However, it should be noted that the scope of the present invention is not limited thereto.

The measurements and evaluations were conducted by the following methods. In the following examples and comparative examples, The term "parts" is based on weight.

(1) Analysis of HPA By Gas Chromatography (GC)

An acetone solution of crude HPA was analyzed using a capillary column (product equivalent to "DB-1" of Agilent Technologies Inc.).

(2) Trans-Isomer Purity of DOG

An acetone solution of DOG was analyzed using a capillary column (product equivalent to "DB-1" of Agilent Technologies Inc.). The trans-isomer purity was calculated from the peak areas of the gas chromatogram.

(3) Average Particle Size of DOG

Measured by a dry method using a laser diffraction particle size distribution analyzer at a dispersion pressure of 20 kPa. The average particle size was calculated based on Fraunhofer diffraction theory.

(4) Water Content of HPA

Wet HPA crystals after washing with water were dried at 20° C. for 20 h under a stream of nitrogen, to measure the decrease in weight. The moisture content of the crystals after drying was measured by Karl Fischer method using a dehydrated pyridine solvent. The water content was determined using the total of the weight decrease and the moisture content.

(5) Water Content of DOG

Wet DOG crystals after washing with water were dried at 85° C. for 20 h in an atmosphere of nitrogen, to measure the decrease in weight. The moisture content of the crystals after drying was measured by Karl Fischer method using dehydrated pyridine solvent. The water content was determined using the total of the weight decrease and the moisture content.

(6) Heat Resistance

In a test tube, 5 g of DOG was placed and the inner atmosphere was replaced by nitrogen. Then, the sample was heated to 140° C. by a block heater. After 20 h of the heating, the trans-isomer purity was determined by GC.

REFERENCE EXAMPLE 1

(1) Synthesis of HPA

To a mixture of 595 parts of isobutylaldehyde (IBD) and 657 parts of 37% by weight formalin, 33 parts of triethylamine (TEA) was added over 5 min at 40° C. with stirring under a stream of nitrogen. The temperature of the reaction liquid reached 65° C. at the time the addition of TEA was completed. The temperature was gradually increased and reached 90° C. after 30 min. The reaction was allowed to continue at 90° C. for 5 min, and then stopped by externally cooling to 60° C. The low boiling components such as non-reacted IBD and TEA and methanol ware removed by distillation at 60 to 70° C. under 53 kPa, to obtain a reaction product solution containing HPA (crude HPA). It was found by GC analysis that the crude HPA contained 62.4% by weight of HPA, 0.26% by weight of IBD, 2.4% by weight of formaldehyde, 0.31% by weight of TEA, 0.64% by weight of neopentyl glycol, 2.0% by weight of mononeopentyl glycol hydroxypivalate, and 28.5% by weight of water.

(2) Purification of HPA

The crude HPA (835 parts) was completely dissolved in 2505 parts of water at 55° C. The solution was gradually cooled with stirring from 55° C. to 32° C. over 5 h and maintained at 32° C. for one hour. The crystals formed were collected by solid-liquid separation using an upper discharge-type centrifugal separator and washed with water, to obtain HPA having a purity of 96.5% by weight in a 60% recovery. The water content was 12% by weight, the residual TEA was 0.01% by weight and the residual formaldehyde was 0.01% by weight.

EXAMPLE 1

DOG Synthesis Using Purified HPA

To a solution of 222 parts of TMP in 1850 parts of water, 48 parts of p-toluenesulfonic acid (PTSA) was added. To the resulting solution, an aqueous solution which had been prepared by dissolving 192 parts of the purified HPA obtained in Reference Example 1 in 90 parts of water at 80° C. was added dropwise over 4 h. X was 15% by weight and the reaction temperature was 70° C. After the dropwise addition, the reaction mixture was aged at 70° C. for 3 h. During the reaction, the pH of the reaction system was 1.3. After the aging, the reaction product liquid was subjected to solid-liquid separation by filtration to obtain 356 parts of wet DOG and 2046 parts of a reaction mother liquor. The wet DOG was washed with water and dried to obtain 285 parts of DOG crystals. The yield of DOG on the basis of the charged TMP was 83 mol %. The obtained DOG crystals had a trans-isomer purity of 98.7% by weight and an average particle size of 17 µm. The amount of the recovered liquid was 3517 parts (reaction mother liquor, recovered washings and water recovered during the drying). The liquid content of the wet DOG crystals immediately after the filtration was 20% by weight.

EXAMPLE 2

(1) First Recycle Reaction

The first recycle reaction was performed in the same manner as in Example 1 except for dissolving 222 parts of TMP in 1897 parts (90% by weight) of the reaction mother liquor obtained in Example 1 and using 1.4 parts of PTSA and 282 parts of the aqueous solution of the purified HPA. During the reaction, the pH of the reaction system was 1.3. The yield of the dried DOG (319 parts) was 93 mol %, the trans-isomer purity was 99.3% by weight, and the average particle size was 17 µm. The liquid content of the wet DOG crystals immediately after the filtration was 20% by weight. The amount of the recovered liquid (recovered washings and water recovered during the drying) except for the reaction mother liquor to be reused was 1480 parts.

(2) Second Recycle Reaction

The second recycle reaction was performed in the same manner as in the first recycle reaction except for using 1854 parts (89% by weight) of the reaction mother liquor obtained in the first recycle reaction and 43 parts of water. During the reaction, the pH of the reaction system was 1.2. The yield of the dried DOG was 93 mol %, the trans-isomer purity was 99.3% by weight, and the average particle size was 17 µm. The liquid content of the wet DOG crystals immediately after the filtration was 20% by weight.

(3) Third and Subsequent Recycle Reactions

The procedures of the second recycle reaction were repeated to perform the third to tenth recycle reactions, in which the yield of DOG was 93 mol %, the trans-isomer purity was 99.3% by weight, and the average particle size was 17 µm, each on average. The amount of the recovered liquid was 1480 parts on average, and the liquid content of the wet DOG crystals immediately after the filtration was 20% by weight on average.

COMPARATIVE EXAMPLE 1

After dissolving 230 parts of TMP in 1850 parts of water, 55 parts of PTSA was added to the resultant solution. The solution was heated to 60° C., and then added dropwise with 288 parts of the crude HPA obtained in Reference Example 1 over 3.5 h. Thereafter, the reaction mixture was aged at 60° C. for 3 h. During the reaction, the pH of the reaction system was 1.5. The reaction product liquid was then subjected to solid-liquid separation by filtration, and the separated DOG crystals were washed with 1400 parts of water and dried. The yield of the dried DOG (285 parts) was 80 mol %, the trans-isomer purity was 95% by weight, and the average particle size was 10 µm. The liquid content of the wet DOG crystals immediately after the filtration was 40% by weight. The amount of the recovered liquid (reaction mother liquor, recovered washings and water recovered during the drying) was 3538 parts.

COMPARATIVE EXAMPLE 2

The reaction was performed in the same manner as in Example 1 except for changing the reaction temperature to 85° C. No crystals were precipitated and an oily product was produced instead. When the reaction mixture was cooled to 60° C. under stirring, DOG crystallized. The crystals were separated by filtration, washed with water, and dried. The trans-isomer purity of the obtained DOG crystals was 85% by weight.

COMPARATIVE EXAMPLE 3

The reaction was performed in the same manner as in Example 1 except for changing the pH during the reaction to 5.0. The trans-isomer purity of the obtained DOG crystals was 98% by weight and the yield was 30 mol %.

COMPARATIVE EXAMPLE 4

The reaction was performed in the same manner as in Example 1 except for charging a reaction vessel with all of HPA, TMP, water and PTSA simultaneously and omitting the dropwise addition of HPA. The trans-isomer purity of the obtained DOG crystals was 95% by weight and the liquid content was 45% by weight.

COMPARATIVE EXAMPLE 5

The reaction was performed in the same manner as in Example 1 except for reducing the amount of water such that X was increased to 40% by weight. The reaction liquid changed to a creamy state as the reaction proceeded to make a sufficient stirring difficult. Although the stirring speed was increased, the reaction liquid could not be stirred sufficiently to the end of reaction. The trans-isomer purity of the obtained DOG crystals was 85% by weight and the liquid content was 45% by weight.

EXAMPLE 3

DOG Synthesis Using Purified HPA

To a solution of 251 parts of TMP in 1920 parts of water, 33 parts of PTSA was added. To the resulting solution, 318 parts of a 60% aqueous solution (70° C.) of the purified HPA prepared in Reference Example 1 was added dropwise over 6 h. X was 15% by weight and the reaction temperature was 70° C. After the dropwise addition, the reaction mixture was aged at 70° C. for one hour. During the reaction, the pH of the reaction system was 1.3. After the aging, the reaction product liquid was subjected to solid-liquid separation by filtration to obtain 446 parts of wet DOG and 2076 parts of a reaction mother liquor. The wet DOG was washed with 1000 parts of water and dried to obtain 339 parts of DOG crystals. The yield of DOG on the basis of the charged TMP was 83 mol %. The obtained DOG crystals had a trans-isomer purity of 98.7% by weight and an average particle size of 17 µm. The amount of the recovered liquid was 3183 parts (reaction mother liquor, recovered washings and water recovered during the drying).

The liquid content of the wet DOG crystals immediately after the filtration was 24% by weight.

EXAMPLE 4

DOG Synthesis Using Seed Crystals

The reaction was performed in the same manner as in Example 3 except for dissolving 236 parts of TMP in 1817 parts of water under heating and using 25 parts of DOG obtained in Example 3 (seed crystals), 33 parts of PTSA, and 299 parts of a 60% aqueous solution (70° C.) of the purified HPA prepared in Reference Example 1. The yield of dried DOG (315 parts exclusive of the seed crystals) was 82 mol %, the trans-isomer purity was 99.6% by weight, and the average particle size was 25 μm. The water content of the DOG crystals immediately after the filtration was 24% by weight.

EXAMPLE 5

Recycle Reaction Using Seed Crystals (1) First Recycle Reaction

The first recycle reaction was performed in the same manner as in Example 4 except for dissolving 177 parts of TMP in 1863 parts (90% by weight) of the reaction mother liquor obtained in Example 4 and 87 parts of water under heating, and using 73 parts of DOG (seed crystals), 3.3 parts of PTSA and 225 parts of a 60% aqueous solution (70° C.) of the purified HPA prepared in Reference Example 1. During the reaction, the pH of the reaction system was 1.3. The yield of the dried DOG (262 parts exclusive of the seed crystals) was 91 mol %, the trans-isomer purity was 99.8% by weight, and the average particle size was 30 μm. The liquid content of the wet DOG crystals immediately after the filtration was 24% by weight. The amount of the recovered liquid (recovered washings and water recovered during the drying) except for the reaction mother liquor to be reused was 1230 parts.

(2) Second Recycle Reaction

The second recycle reaction was performed in the same manner as in the first recycle reaction except for dissolving 177 parts of TMP in 1863 parts (89% by weight) of the reaction mother liquor obtained in the first recycle reaction and 87 parts of water under heating. During the reaction, the pH of the reaction system was 1.3. The yield of the dried DOG was 91 mol %, the trans-isomer purity was 99.8% by weight, and the average particle size was 30 μm. The liquid content of the wet DOG crystals immediately after the filtration was 24% by weight.

(3) Third and Subsequent Recycle Reactions

The procedures of the second recycle reaction were repeated to perform the third to tenth recycle reactions, in which the yield of DOG was 91 mol %, the trans-isomer purity was 99.8% by weight, and the average particle size was 30 μm, each on average. The amount of the recovered liquid was 1230 parts on average, and the liquid content of the wet DOG crystals immediately after the filtration was 24% by weight on average.

EXAMPLE 6

Recycle Reaction Using Seed Crystals

A recycle reaction was performed in the same manner as in the first recycle reaction of Example 5 to prepare a reaction product solution, which was then subjected to a solid-liquid separation into DOG crystals and a reaction mother liquor. Then the next recycle reaction was performed in the same manner as in Example 5 except for dissolving 177 parts of TMP in a mixture of 487 parts of the reaction product liquid (containing 73 parts of DOG (seed crystals), and corresponding to 20% by weight of the reaction product liquid and 20% by weight of the reaction mother liquor), 1449 parts (70% by weight) of the reaction mother liquor, and 87 parts of water. During the reaction, the pH of the reaction system was 1.3. The yield of the dried DOG was 91 mol %, the trans-isomer purity was 99.8% by weight, and the average particle size was 30 μm. The liquid content of the wet DOG crystals immediately after the filtration was 24% by weight. The amount of the recovered liquid (recovered washings and water recovered during the drying) except for the reaction mother liquor to be reused was 1230 parts.

COMPARATIVE EXAMPLE 6

The reaction was performed in the same manner as in Example 4 except for changing the reaction temperature to 55° C. The trans-isomer purity of DOG crystals was 99.0% by weight, the yield was 80 mol %, and the average particle size was 10 μm. The water content of the wet DOG crystals immediately after the filtration was 40% by weight. The amount of the recovered liquid was 3146 parts (reaction mother liquor, recovered washings and water recovered during the drying).

COMPARATIVE EXAMPLE 7

The reaction was performed in the same manner as in Example 4 except for changing the reaction temperature to 85° C. No crystals were precipitated and an oily product was produced instead. When the reaction mixture was cooled to 65° C. under stirring, DOG crystallized. The crystals were separated by filtration, washed with water, and dried. The trans-isomer purity of the obtained DOG crystals was 85% by weight.

COMPARATIVE EXAMPLE 8

The reaction was performed in the same manner as in Example 4 except for changing the pH during the reaction to 5.0. The trans-isomer purity of the obtained DOG crystals was 98.0% by weight and the yield was 30 mol %.

COMPARATIVE EXAMPLE 9

The reaction was performed in the same manner as in Example 4 except for charging a reaction vessel with all of HPA, TMP, water and PTSA simultaneously and omitting the dropwise addition of HPA. The trans-isomer purity of the obtained DOG crystals was 95.0% by weight and the liquid content was 45% by weight.

COMPARATIVE EXAMPLE 10

The reaction was performed in the same manner as in Example 4 except for reducing the amount of water such that X' was increased to 40% by weight. The reaction liquid changed to a creamy state as the reaction proceeded to make the sufficient stirring difficult. Although the stirring speed was increased, the reaction liquid could not be stirred sufficiently to the end of reaction. The trans-isomer purity of the obtained DOG crystals was 85.0% by weight and the liquid content was 45% by weight.

EXAMPLE 7

After adding 100 parts of concentrated hydrochloric acid to a solution of 916 parts of TMP in 3825 parts of water, the resultant solution was heated to 60° C. To the solution, the crude HPA prepared in Reference Example 1 was added dropwise over 3 h while maintaining the reaction temperature at 60° C. After the addition, the reaction mixture was aged for 2 h at 60° C. After the aging, the reaction product liquid was cooled to 40° C. and subjected to solid-liquid separation by vacuum filtration to separate DOG crystals, which were then sprayed with 750 parts of a 1% aqueous solution of sodium carbonate. The pH of the recovered basic solution was 9. After washing with 1520 parts of water and drying, 1267 parts of DOG crystals was obtained. The yield of DOG on the basis of the charged TMP was 85 mol %. The trans-isomer purity was 99.5% by weight, while 99.4% by weight after the heat resistance test.

EXAMPLE 8

The procedures of Example 7 were repeated except for washing DOG crystals with 75000 parts of a 10 ppm aqueous solution of sodium carbonate. The pH of the recovered basic solution was 8.0. The yield of DOG on the basis of the charged TMP was 84 mol %. The trans-isomer purity was 99.3% by weight, while 99.2% by weight after the heat resistance test.

EXAMPLE 9

The procedures of Example 7 were repeated except for washing DOG crystals with 16 parts of a 48% aqueous solution of sodium hydroxide. The pH of the recovered basic solution was 12. The yield of DOG on the basis of the charged TMP was 86 mol %. The trans-isomer purity was 99.3% by weight, while 99.1% by weight after the heat resistance test.

EXAMPLE 10

The procedures of Example 7 were repeated except for omitting the washing with the 1% aqueous solution of sodium carbonate, to obtain 1267 parts of DOG crystals. The pH of the recovered filtrate (mother liquor) was 2.5. The yield of DOG on the basis of the charged TMP was 85 mol %. The trans-isomer purity was 99.3% by weight, while 47.8% by weight after the heat resistance test.

A part of DOG crystals was stirred in distilled water such that the mother liquor in DOG crystals and the distilled water were mixed uniformly and then filtered. The amount of acid in the filtrate was determined by the titration with an alkali. From the result, the amount of acid in DOG crystals was calculated.

A 2000-ml three-necked flask equipped with a stirrer and a reflux condenser was charged with 400 parts of DOG crystals, 1598 parts of water, and 2 parts of sodium hydrogen carbonate (corresponding to about 1.2 times by mole of the amount of the acid in DOG crystals). The mixture was stirred at 70° C. for 2 h and then vacuum-filtered. The pH of the recovered basic solution was 8.9. After washing with water and drying, DOG crystals were obtained in a recovery of 98% by weight. The trans-isomer purity was 99.3% by weight, while 99.0% by weight after the heat resistance test.

EXAMPLE 11

In the same manner as in Example 10, DOG crystals were obtained. A 2000-ml three-necked flask equipped with a stirrer and a reflux condenser was charged with 400 parts of DOG crystals and 1600 parts of water. The mixture was stirred at 70° C. for 2 h and then vacuum-filtered. The pH of the recovered basic solution was 5.8. After washing with water and drying, DOG crystals were obtained in a recovery of 98% by weight. The trans-isomer purity was 99.3% by weight, while 62.6% by weight after the heat resistance test.

The water-washed DOG crystals were further washed with the basic solution in the same manner as in Example 10. The trans-isomer purity after the heat resistance test was 99.1% by weight.

EXAMPLE 12

In the same manner as in Example 10, DOG crystals were obtained. A 2000-ml three-necked flask equipped with a stirrer and a reflux condenser was charged with 160 parts of DOG crystals and 1600 parts of toluene. The mixture was heated to 90° C. for complete dissolution. The solution was slowly cooled to 40° C. over 6 h and then vacuum-filtered. After washing with toluene and drying, DOG crystals were obtained in a recovery of 90% by weight. The trans-isomer purity was 100% by weight, while 66.3% by weight after the heat resistance test.

The toluene-washed DOG crystals were further washed with the basic solution in the same manner as in Example 10. The trans-isomer purity after the heat resistance test was 99.2% by weight.

The high purity DOG obtained by the process of the present invention is useful as an intermediate or monomer for the production of polymeric materials such as poly(meth)acrylate, polycarbonate, polyester, polyurethane, polyether polyol and epoxy resin, as well as, a raw material for the production of photo-curable resin, adhesive, photo-curable ink, plasticizer, resin stabilizer, lubricant oil, paint, etc.

What is claimed is:

1. A process of producing a dioxane glycol represented by the following formula I:

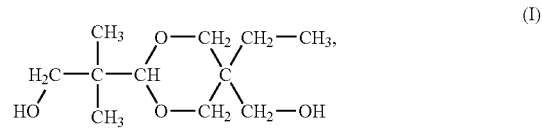

which comprises a step of allowing hydroxypivalaldehyde represented by the following formula II:

to react with trimethylolpropane represented by the following formula III:

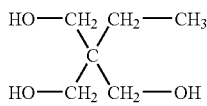 (III)

in water in the presence of an acid catalyst,
the reaction of hydroxypivalaldehyde and trimethylolpropane being performed under conditions which meet the following requirements:
(A) a total amount of amines and/or amine salts in hydroxypivalaldehyde is 1.5% by weight or less;
(B) the reaction is performed at from 65 to 80° C.;
(C) pH of a reaction system is kept within a range of from 0.1 to 4.0 during the reaction;
(D) X represented by the following formula IV:

$$X(\% \text{ by weight}) = B/A \times 100 \qquad (IV)$$

wherein A is a total weight of hydroxypivalaldehyde, trimethylolpropane, water and the acid catalyst which are supplied to the reaction system, and B is a theoretical amount of the dioxane glycol to be produced from hydroxypivalaldehyde and trimethylolpropane which are supplied to the reaction system, is from 3 to 35% by weight; and
(E) a solid or solution of at least one of trimethylolpropane and hydroxypivalaldehyde is added to (a) at least one of hydroxypivalaldehyde and trimethylolpropane, (b) water and (c) the acid catalyst in a reaction vessel over a time period of 0.5 to 24 h.

2. The process according to claim 1, wherein the amine is triethylamine and the amine salt is triethylammonium formate.

3. The process according to claim 1, further comprising a step of separating a reaction product liquid after the reaction into crystals of the dioxane glycol and a reaction mother liquor.

4. The process according to claim 3, wherein the separation of the reaction product liquid is performed in a pH range of from 0.1 to 4.0.

5. The process according to claim 3, wherein 98% by weight or less of the reaction mother liquor is reused in subsequent reactions for the production of the dioxane glycol.

6. The process according to claim 3, wherein the crystals of the dioxane glycol are washed with a basic solution.

7. The process according to claim 6, wherein the basic solution is a solution of an inorganic base in water and/or an organic solvent.

8. The process according to claim 7, wherein a concentration of the base in the basic solution is from 10ppm to 50% by weight.

9. The process according to claim 1, wherein the reaction of trimethylolpropane and hydroxypivalaldehyde is performed in the presence of seed crystals in addition to the acid catalyst under conditions which further meet a requirement that X' represented by the following formula V:

$$X'(\% \text{ by weight}) = B'/A' = 100 \qquad (V)$$

wherein A' is a total weight of hydroxypivalaldehyde, trimethylolpropane, the acid catalyst, water and the seed crystals which are supplied to the reaction system, and B' is a total weight of a theoretical amount of the dioxane glycol to be produced from hydroxypivalaldehyde and trimethylolpropane which are supplied to the reaction system and a weight of DOG contained in the seed crystals, is from 3 to 35% by weight.

10. The process according to claim 9, wherein the seed crystals are added in an amount of from 0.1 to 30% by weight based on a total amount of hydroxypivalaldehyde, trimethylolpropane, the acid catalyst, the seed crystals and water.

11. The process according to claim 9, wherein a reaction product liquid is separated into crystals of the dioxane glycol and a reaction mother liquor, and 98% by weight or less of the reaction mother liquor is reused in subsequent reactions for the production of the dioxane glycol.

12. The process according to claim 9, wherein a part of reaction product solution which contains the seed crystals in an amount of from 0.1 to 30% by weight based on a total amount of hydroxypivalaldehyde, trimethylolpropane, the acid catalyst, the seed crystals and water is added to the reaction system.

13. The process according to claim 9, wherein the seed crystals are crystals of the dioxane glycol of the formula I.

14. The process according to claim 1, wherein the at least one of trimethylolpropane and hydroxypivalaldehyde is added to (a) the at least one of hydroxypivalaldehyde and trimethylolpropane, (b) water and (c) the acid catalyst, continuously.

15. The process according to claim 14, wherein the at least one of trimethylolpropane and hydroxypivalaldehyde is added to (a) the at least one of hydroxypivalaldehyde and trimethylolpropane, (b) water and (c) the acid catalyst, dropwise.

* * * * *